(12) United States Patent
Boehm et al.

(10) Patent No.: US 8,113,194 B2
(45) Date of Patent: Feb. 14, 2012

(54) BREATH-CONTROLLED INHALATION THERAPY DEVICE

(75) Inventors: Andreas Boehm, Reichling (DE); Martin Luber, Munich (DE)

(73) Assignee: PARI GmbH Spezialisten für effektive Inhalation, Starnberg (DE)

( * ) Notice: Subject to any disclaimer, the term of this patent is extended or adjusted under 35 U.S.C. 154(b) by 638 days.

(21) Appl. No.: 11/921,206

(22) PCT Filed: May 15, 2006

(86) PCT No.: PCT/EP2006/004540
§ 371 (c)(1),
(2), (4) Date: Mar. 17, 2009

(87) PCT Pub. No.: WO2006/128567
PCT Pub. Date: Dec. 7, 2006

(65) Prior Publication Data
US 2009/0217923 A1    Sep. 3, 2009

(30) Foreign Application Priority Data
May 31, 2005    (DE) .................. 10 2005 024 779

(51) Int. Cl.
*A61M 11/00* (2006.01)
*B05B 1/26* (2006.01)

(52) U.S. Cl. ......... 128/200.18; 128/200.14; 128/200.21; 128/203.12; 128/203.15; 128/204.14

(58) Field of Classification Search ............. 128/200.14, 128/200.18, 200.21, 200.23, 203.12, 203.15, 128/204.14
See application file for complete search history.

(56) References Cited

U.S. PATENT DOCUMENTS

| 5,054,477 A | * | 10/1991 | Terada et al. ............ 128/200.14 |
| 5,511,538 A | | 4/1996 | Haber et al. |
| 5,584,285 A | * | 12/1996 | Salter et al. .............. 128/200.21 |
| 5,823,179 A | * | 10/1998 | Grychowski et al. .... 128/200.18 |
| 6,105,929 A | * | 8/2000 | Davenport et al. .......... 251/63.6 |
| 2002/0157663 A1 | | 10/2002 | Blacker et al. |
| 2004/0173209 A1 | | 9/2004 | Grychowski et al. |

FOREIGN PATENT DOCUMENTS

JP    63-080866    4/1988

* cited by examiner

*Primary Examiner* — Loan Thanh
*Assistant Examiner* — Kathryn D Sheikh
(74) *Attorney, Agent, or Firm* — Wolf, Greenfield & Sacks, P.C.

(57) ABSTRACT

A breath-controlled inhalation therapy device includes an obturation mechanism, obturating a nozzle opening through which a pressurized gas, preferably pressurized air, is issued when the device is in operation. An actuation mechanism actuates the obturation mechanism only in the exhalation phases of the respiration cycle of a patient. The fluid to be atomized is therefore substantially atomized only in the inhalation phases.

18 Claims, 9 Drawing Sheets

BREATH-CONTROLLED INHALATION THERAPY DEVICE

The invention relates to a breath-controlled inhalation therapy device for the provision of an aerosol for use by a patient as part of an inhalation therapy.

A device of the type described above is known, for example, from US 2004/1073209 A. In this device, an aerosol is generated using a nozzle, in that a compressed gas, for example compressed air, flowing out of a nozzle opening draws a liquid to be nebulised through inlet channels and nebulises it upon exit out of outlet openings adjacent to the nozzle opening. A baffle is disposed in front of the nozzle, which, during a nebulising operation, is disposed close to the nozzle openings in the inhalation phases and ensures that the exiting compressed gas is diverted, which causes the drawing and nebulising action on the liquid to be nebulised. The baffle is shiftable and is moved away from the nozzle openings during the exhalation phases such that nebulisation no longer takes place, even if the compressed gas continues to flow out of the nozzle opening. Breath control is thereby achieved in the known device since it is only in the inhalation phases that the baffle is positioned close enough to the nozzle openings to cause nebulisation.

Breath control is generally used in inhalation therapy nebulisers so as to prevent the loss of medicament or aerosol during exhalation phases.

The aim of the invention is to further improve the breath-controlled inhalation therapy devices.

This aim is achieved by means of a breath-controlled inhalation therapy device for the provision of an aerosol for use by a patient as part of an inhalation therapy, said device comprising a housing that defines a nebulisation area, a nozzle opening for the entry of a pressurised gas, preferably compressed air, into the nebulisation area, at least one outlet opening for the entry of a liquid to be nebulised, preferably a therapeutically effective liquid, into the nebulisation area, an closing means for closing the nozzle opening, which is arranged in the nebulisation area relative to the nozzle opening in such a manner that the closing means can be moved into a position closing the nozzle opening and into a position unblocking the nozzle opening, and an actuation device for actuating the closing means in response to the respiratory cycle of the patient so as to actuate the closing means during the exhalation phase of a respiratory cycle of the patient such that the closing means assumes the position closing the nozzle opening.

The invention thereby makes use of the advantageous circumstance that owing to the closing of the nozzle opening for the compressed gas, nebulisation is on the one hand reliably stopped and on the other hand, owing to the resistance generated for the compressed gas source, there is normally an increase in pressure and buffering of compressed gas, which is temporarily available for nebulisation following reopening of the nozzle opening. This circumstance can be used, on the one hand, in larger therapy devices to improve efficiency, even though these devices can already be designed in a very efficient manner owing to their size. On the other hand, smaller therapy devices can be realised, which reach the efficiency of the larger devices at a smaller size.

In a simple yet advantageous embodiment, the closing means is disposed opposite the nozzle opening. The required movement can thereby be effected in a simple manner.

In the position exposing the nozzle opening, the closing means advantageously forms a baffle for the compressed gas exiting from the nozzle opening and the liquid exiting from the outlet opening. The closing means is therefore accorded a dual function which can be realised without any problems in one and the same component of the device according to the invention. No additional baffles or gas flow control is therefore required according to the invention. However, these elements can be additionally provided.

In an alternative design, the closing means is disposed to the side of the nozzle opening.

The device according the invention can thereby be designed in such a manner that the closing means for closing the nozzle opening acts on a nozzle body consisting of a soft, flexible material, in which the nozzle opening is formed.

In order to achieve the best results as regards the sealing of the nozzle opening for the compressed gas, which is important for the invention, the closing means is advantageously made, at least partly, out of a soft and flexible material. Alternatively or additionally, a sealing portion made of a soft and flexible material can be provided at the nozzle opening.

In order to ensure movement of the closing means, the actuation device advantageously comprises a connecting means that connects the actuation device to the closing means. In this manner, arrangement of the actuation device in the inhalation therapy device according to the invention can take place with more freedom. If the actuation device and the closing means are disposed close to one another, the connecting member of the actuation device can also be realised such that it is very small or can be dispensed with completely.

Particularly suitable for breath control is an actuation device comprising a piston member, with the pressure prevailing in the housing determining the position of the piston member.

In order to bring the piston into a defined position, the actuation device advantageously comprises a spring member that determines the rest position of the piston member.

In an advantageous embodiment, the actuation device comprises a cylindrical member in which the piston can move. The spring member is thereby disposed in the compression space that is enclosed by the piston member and the cylindrical member. It is furthermore advantageous for the cylindrical member to be formed by the housing.

Since the closing means has to be moved, the connecting means is connected to the piston member since the piston member constitutes the element of the actuation device that moves depending on breath.

Since an indication of the position of the closing means is desirable, the connecting means is advantageously extended beyond the piston member such that the connecting member protrudes out of the housing. The position of the protruding part is thus an indicator for the position of the closing means.

In order to prevent a counter-pressure in the compression space between the piston and the cylinder of the actuation device, which could hinder movement, a ventilation passage is preferably provided for the inlet of air to and outlet of air from the space enclosed by the piston member and the cylindrical member during movement of the piston member in the cylindrical member.

In order to mechanically ensure and stabilise the movement of the piston and the transmission of movement to the closing means, the actuation device preferably comprises a guide member in which the connecting member is disposed.

In an embodiment that is favourable in terms of manufacturing technology, the connecting member is formed integrally with the closing means.

In inhalation therapy devices having a supply air duct, the actuation device is preferably disposed therein. The available space is therefore optimally used and the actuation device is accommodated such that it is protected.

The invention will be described in more detail in the following by means of embodiments and with reference to the drawings in which.

FIGS. 9 A/B show a partial area of a further embodiment of an inhalation therapy device according the invention; and FIGS. 10 A/B show a further embodiment of an inhalation therapy device according to the invention.

Figure 1:
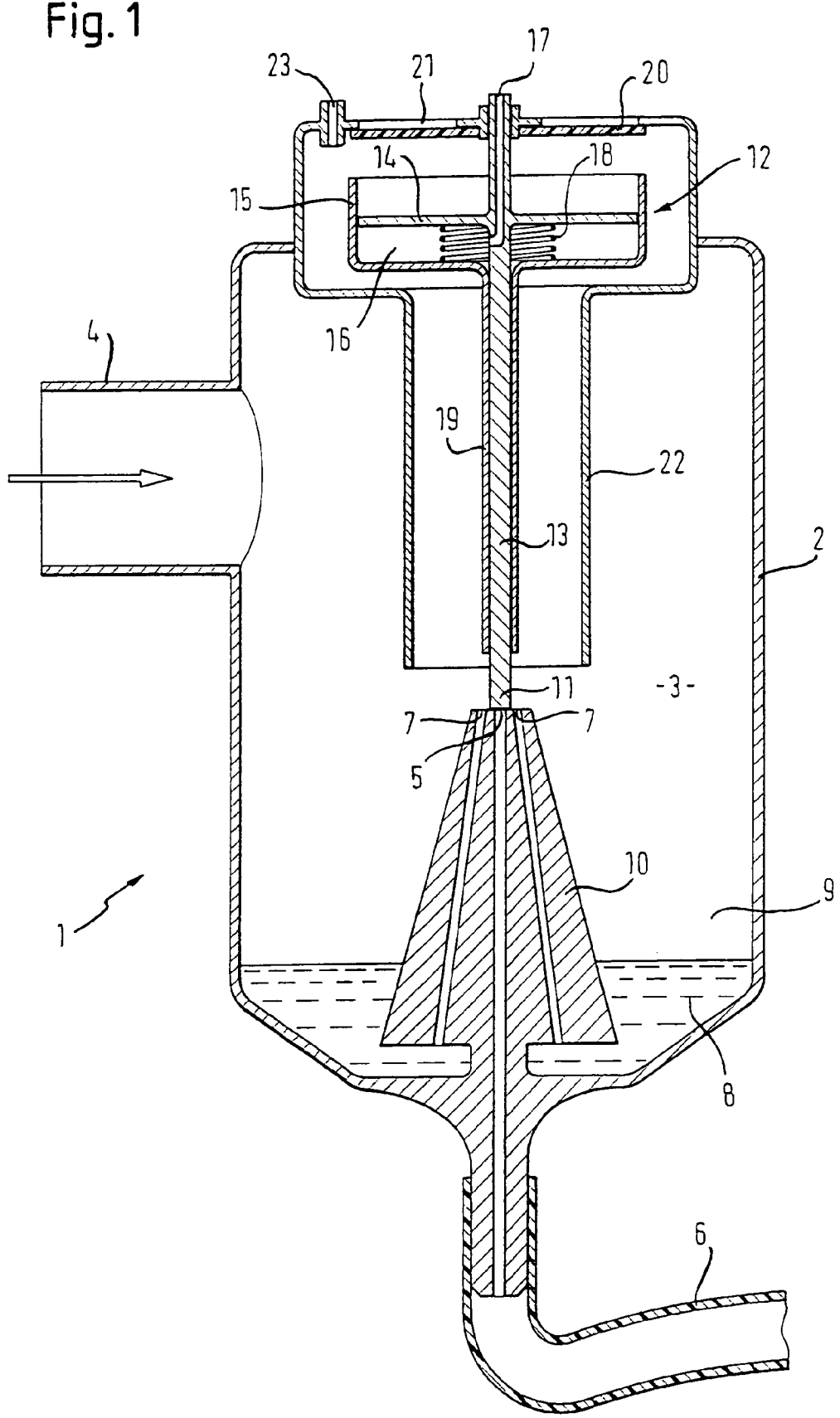
FIG. 1 shows a schematic sectional view of an embodiment of an inhalation therapy device according to the invention.

FIG. 1 shows an inhalation therapy device 1 according to the invention for the provision of an aerosol for use by a patient as part of an inhalation therapy. In the embodiment shown in FIG. 1, the inhalation therapy device 1 comprises a housing 2 that defines a nebulisation area 3 in the interior thereof. During operation, an aerosol is generated in the inhalation area 3 and is provided to a patient for inhalation. The patient inhales the aerosol via a mouthpiece 4 that is provided on the inhalation therapy device 1 and is connected to the interior 3 of the housing 2. Furthermore, in the embodiment shown in FIG. 1, at least one nozzle opening 5 is provided in the nebulisation area 3, out of which a pressurised gas, preferably compressed air, exits during operation and enters the nebulisation area 3. The compressed gas or compressed air is supplied via a supply line 6 to the device 1 from a compressed air source, preferably a compressor, which is not shown in FIG. 1.

In the embodiment shown in FIG. 1, at least one outlet opening 7 is arranged adjacent to the nozzle opening 5 for the compressed gas, out of which a liquid to be nebulised, preferably a therapeutically effective liquid, exits during operation and enters the nebulisation area 3. The liquid 8 to be nebulised is stored in a liquid reservoir 9 of the device 1, said reservoir 9 preferably forming part of the housing 2, as illustrated in the embodiment shown in FIG. 1. Since the liquid outlet opening 7 is arranged adjacent to the nozzle opening 5, the compressed gas exiting out of the nozzle opening causes nebulisation of the liquid exiting out of the outlet opening. An effect is thereby preferably used, by means of which the liquid 8 to be nebulised is drawn through the inlet opening 7 owing alone to the fact that the compressed gas flows out of the nozzle opening 5 and generates a negative pressure at the outlet opening 7 for the liquid. Owing to the spatial proximity of the compressed gas nozzle opening 5 and the liquid outlet opening 7 that is required herefor, the compressed gas nozzle opening 5 and the liquid outlet opening 7 are accommodated in the shown embodiment in a nozzle body 10, which extends into the reservoir 9 and the liquid 8 stored therein. The embodiment shown in FIG. 1 is also particularly advantageous because not just one but two symmetrically arranged outlet openings 7 for the liquid 8 are provided adjacent to the nozzle opening 5. Another advantageous embodiment comprises an annular gap or annular groove surrounding the nozzle opening, which opens adjacent to the nozzle opening 5.

In accordance with the invention, an closing means 11 is provided inside the housing 3 in the embodiment shown in FIG. 1. The closing means 11 closes the nozzle opening 5, for which purpose the closing means 11 is disposed opposite the nozzle opening 5 in the nebulisation area 3. The closing means 11 can assume a position exposing the nozzle opening and a position closing the nozzle opening.

In FIG. 1, the closing means 11 is shown in the position closing the nozzle opening. In this position, the closing means 11 prevents the compressed gas from exiting out of the nozzle opening 5 and thus the liquid 8 does not exit from the outlet openings 7 and is not nebulised either. Since the nozzle opening 5 is blocked, the pressure in the supply line 6 increases because the compressed gas source, for example the aforementioned compressor, continues to supply the compressed gas, however now against the resistance of the blocked nozzle opening 5.

Figure 2:
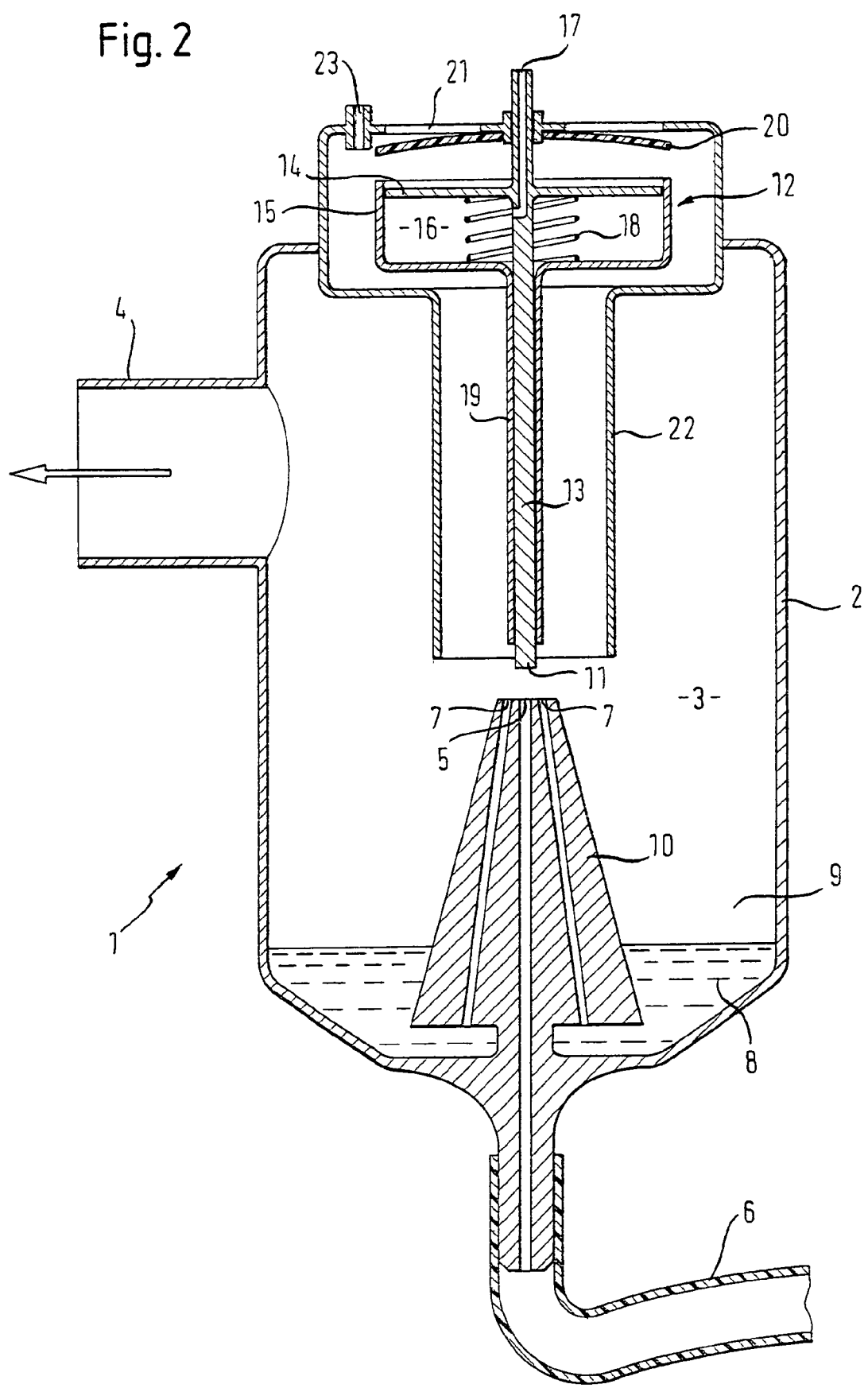
FIG. 2 shows a further schematic sectional view of the embodiment of FIG. 1.

In FIG. 2, the closing means 11 is shown in the position exposing the nozzle opening; FIG. 2 otherwise corresponds to FIG. 1 and thus reference can inasmuch be made at this point to the description of FIG. 1. In the position exposing the nozzle opening, the closing means 11 is at a distance from the nozzle opening 5 for compressed gas such that compressed gas supplied via the supply line exits out of the nozzle opening 5 and liquid exiting out of the outlet opening is nebulised. The pressure in the supply line 6 thereby decreases to the operating pressure that is provided by the compressed gas source, for example the aforementioned compressor.

In a preferred design of the device 1 according to the invention, the closing means 11, when in the position exposing the nozzle opening, also acts as a baffle, upon which the exiting compressed gas and nebulised liquid impinge. The advantageous effects of such baffles, which are also referred to as gas flow controls, in the outlet area of openings 5 and 7 of the nebuliser nozzle 10 are known to the person skilled in the art. By designing the known gas flow control so as to be moveable between a position exposing the nozzle opening and a position closing the nozzle opening in order to act as an closing means 11, a particularly advantageous design of the inhalation therapy device 1 according to the invention is achieved.

In order to bring the closing means 11 into the position closing the nozzle opening during the patient's exhalation phases in accordance with the invention, an actuation device 12 is provided in the embodiment shown in FIGS. 1 and 2 to cause movement of the closing means 11 out of the position exposing the nozzle opening and into the position closing the nozzle opening. The actuation device 12 thereby responds to the respiratory cycle of the patient in order to actuate the closing means 11 during the exhalation phase of a respiratory cycle of the patient such that the nozzle opening 5 is blocked.

It is achieved according to the invention owing to the cooperation of the closing means 11 and the actuation device 12 that aerosol generation is interrupted during the exhalation phases of the respiratory cycle of a patient and that aerosol is provided to the patient during the inhalation phases. Different positive effects are thereby achieved as a result of interrupting aerosol generation according to the invention by closing the nozzle opening 5 for the compressed gas. Aerosol production is on the one hand immediately interrupted without the reaction times of the compressed gas source, for example the compressor, leading to undesirable delays. The closing means acts so quickly on the nozzle opening 5 that interruption occurs almost instantly. On the other hand, in the advantageous case that the exiting compressed gas draws the liquid to be nebulised, exiting of the liquid 8 to be nebulised also stops almost simultaneously with the interruption of the exiting of the compressed gas since the drawing action on the liquid 8 also ceases to apply just as instantly as the flow of compressed gas is interrupted. Finally, blocking of the nozzle opening leads to a pressure increase in the supply line 6, which results in improved aerosol production following reopening of the nozzle opening. This is because an increased pressure and an amount of compressed air buffered in the supply line are available for a short time following reopening.

The actuation device can be realised in different manners.

In the embodiment shown in FIG. 1, the actuation device 12 comprises a connecting member 13 that is on the one hand connected with the closing means 11 and on the other hand with a piston member 14. The piston member 14 is disposed in a cylindrical member 15 so as to enclose a compression space 16 that is ventilated by a ventilation passage 17. Furthermore, a spring member 18 is disposed in the compression space 16, which brings the piston member 14 into a defined rest position.

If the piston member 14 is in the rest position that it assumes owing to the action of the spring member 18, the closing means 11 is then in the position exposing the nozzle opening since the piston member 14 is connected to the closing means 11 via the connecting member 13. This positioning of the piston member 14, the connecting member 13 and the closing means 11 is shown in FIG. 2.

If the patient exhales into the housing 2 of the inhalation therapy device 1 according to the invention, the pressure in the nebulisation area 3 increases since an inhalation valve member 20, which is configured in the shown embodiment as a flat annular disk made of a flexible material, closes an inlet opening 21 for ambient air. Owing to the increase in pressure, the piston member 14 is shifted against the action of the spring member 18 in such a manner that the closing means 11 is moved via the connecting member 13 into the position closing the nozzle opening. This positioning of the piston member 14, the connecting member 13 and the closing means 11 is shown in FIG. 1.

The ventilation passage 17 allows the air present in the compression space 16 to escape when the piston member 14 is moved out of the rest position. Furthermore, ambient air subsequently flows through the ventilation passage 17 into the compression space 16 when the piston member returns to the rest position. It is therefore achieved by means of the ventilation passage 17 that the forces required for movement of the piston member and thus the pressure that causes movement of the piston member 14 can be defined very precisely by means of the spring member 18.

As shown in FIGS. 1 and 2, the connecting member 13 is preferably arranged in the shown embodiment in a guide member 19, which is attached to the cylindrical member 15 and is preferably configured integrally therewith. Owing to the guide member 19, a stable guiding of the connecting member 13 is achieved on the one hand, so that reliable transmission of the movement of the piston member 14 of the actuation device 12 to the closing means 11 occurs. On the other hand, the guide member 19 facilitates sealing of the compression space 16 of the actuation device 12. A corresponding sealing of the compression space 16 is additionally also to be ensured at the contact point between the cylindrical member 15 and the piston member 14.

In the shown embodiment, the connecting member 13 is extended beyond the position of the piston member 14. The ventilation channel 17 is preferably also formed in this section. The connecting member 13 therefore protrudes out of the housing 2 and thereby serves as a visual indicator for the position of the closing means 11.

In the embodiment shown in FIGS. 1 and 2, the actuation device 12 is advantageously disposed in a supply air duct 22 of the inhalation therapy device 1, via which supply air, which flows in from the environment through the inlet openings 21 when the inhalation valve is open during the inhalation phases of the patient, is guided into an area in the direct vicinity of the nozzle opening 5 and the outlet openings 7. The closing means 11 is also located here, which is moved to and fro between the two positions by the connecting means 13 depending on the respiratory cycle of the patient.

In the embodiment shown in FIGS. 1 and 2, a respiratory air outlet opening 23 is advantageously provided, via which the air exhaled into the device can escape from the housing 2 during exhalation phases. The pressure that builds up in the interior of the housing during exhalation and that is required for movement of the closing means 11 can be defined by the design of the shape, the progression and the diameter of the respiratory air outlet opening 23. It must be noted in this regard that a positive influence on the inhalation therapy is also possible in this manner since often an increased expiration resistance is desired. It is furthermore possible in this manner, in coordination with the applied spring force of the spring member 18, to also define the pressure at which the closing means 11 is moved back into the position exposing the nozzle opening. The time of exposure can thus be set just before the start of the inhalation phase, i.e. still in the exhalation phase, such that sufficient aerosol is provided to the patient already at the start of the inhalation phase.

In the embodiment shown in FIGS. 1 and 2, the closing means 11 is formed integrally with the connecting member 13 of the actuation device 12. An alternative design is provided in FIG. 3, which shows a section of the representation in FIGS. 1 and 2 in the region of the openings of the nozzle body 10. According thereto, the closing means 11 is not produced integrally with the connecting means. This design is advantageous insofar as the material of the closing means 11 can be selected independently of the material of the connecting member 13. In order to ensure a good sealing of the nozzle opening 5, the closing means 11, or the part thereof that comes into contact with the nozzle body 10 at the nozzle opening 5, is preferably made from a comparatively soft and flexible material. Soft and flexible materials are often not suitable for producing the connecting member 13 that has to be rigid for the action on the closing means 13 and the transmission of forces associated therewith.

Figure 3:
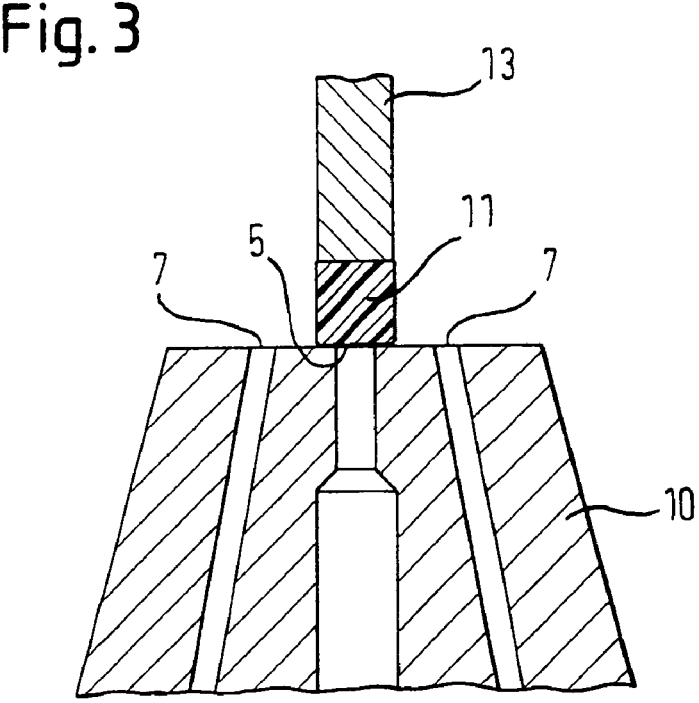
FIG. 3 shows a detailed representation of an advantageous design of the closing means of an inhalation therapy device according to the invention.
Figure 4:
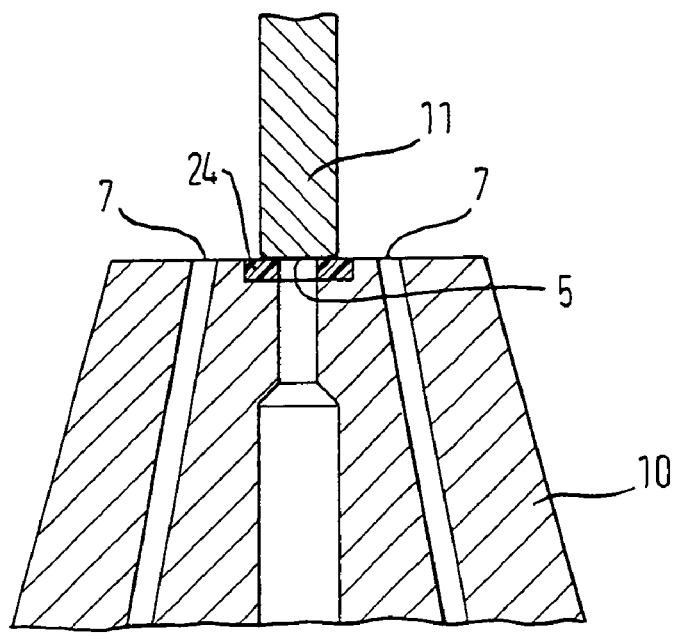
FIG. 4 shows a detailed representation of an advantageous design of the nozzle opening of an inhalation therapy device according to the invention.

FIG. 4 shows a design according to the invention, in which a sealing portion 24 made of a soft, flexible material is provided on the nozzle body 10. Just like in the design according to FIG. 3 as described above, a very good seal is achieved in this manner.

A soft and flexible material can obviously be provided on both the closing means 11 and the nozzle opening 5, which corresponds to a combination of the two designs of FIGS. 3 and 4.

Figure 5:
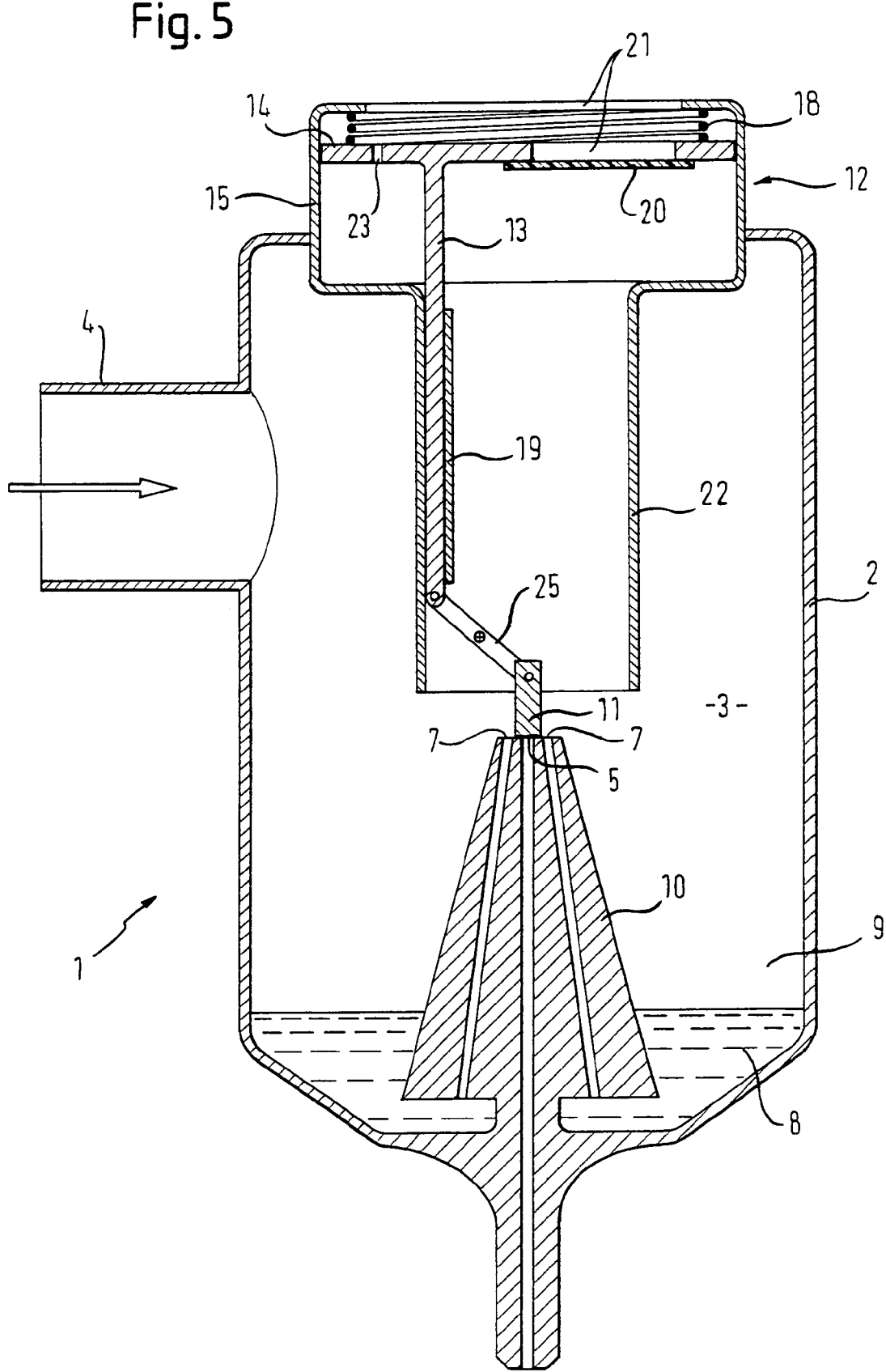
FIG. 5 shows a schematic sectional view of a further embodiment of an inhalation therapy device according to the invention.
Figure 6:
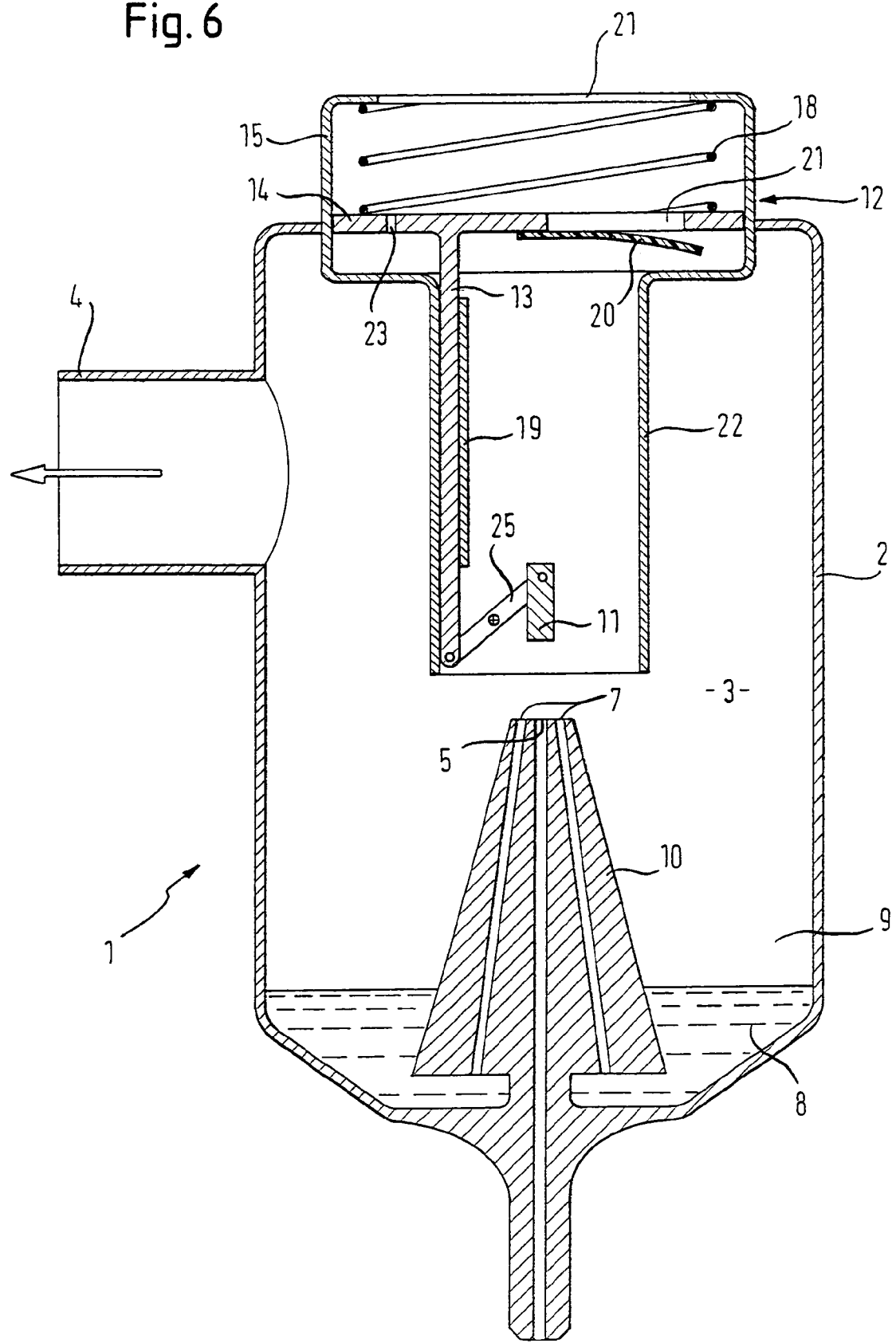
FIG. 6 shows a further schematic sectional view of the embodiment of FIG. 5.

FIGS. 5 and 6 show a further embodiment of an inhalation therapy device 1 according to the invention. An closing means 11 that can assume a position blocking the nozzle opening, as shown in FIG. 5, and a position exposing the nozzle opening, as shown in FIG. 6, is also provided in this embodiment, the structure of which corresponds in many aspects to the embodiment described above such that reference can be made to the previous description. The closing means 11 is moved from one position into the other and back again by an actuation device 12.

The actuation device 12 comprises a connecting member 13 and a piston member 14, which is connected to the connecting member 13 and is disposed in a cylindrical member 15. Differing from the embodiment described above, the piston member is equipped with an inlet opening 21 in the embodiment according to FIGS. 5 and 6, which allows ambient air to flow into the interior of the inhalation therapy device 1 during the inhalation phases. The inlet opening 21 is closed during the exhalation phases by a valve member 20; only a respiratory air outlet opening 23 in the piston member 14, which is preferably provided, allows respiratory air to escape under precisely defined conditions. It is thus ensured, for example, that there is sufficient pressure inside the device during the exhalation phase to shift the piston member 14 in the cylindrical member 15 into the position shown in FIG. 5. The piston member 14 assumes this position against the reset force of a spring member 18 which otherwise moves the piston member 14 into the position shown in FIG. 6.

Since, in the embodiment according to FIGS. 5 and 6, the connecting member 13 is connected to the closing means 11 via a reversing element 25, the closing means 11 assumes the position closing the nozzle opening according to FIG. 5 when the patient exhales into the inhalation therapy device. On the other hand, the closing means 11 is moved into the position exposing the nozzle opening, as shown in FIG. 6, when the patient inhales since the piston member 14 is moved into the rest position owing to the action of the spring member 18. The result of this is that the connecting member 13 moves the closing means 11 via the reversing element 25 into the position exposing the nozzle opening.

In the embodiment shown in FIGS. 5 and 6, part of the housing 2 can replace the cylindrical member 15 since the piston member 14 can obviously also easily perform the shifting movement along the inner wall of the housing 2.

Figure 7:
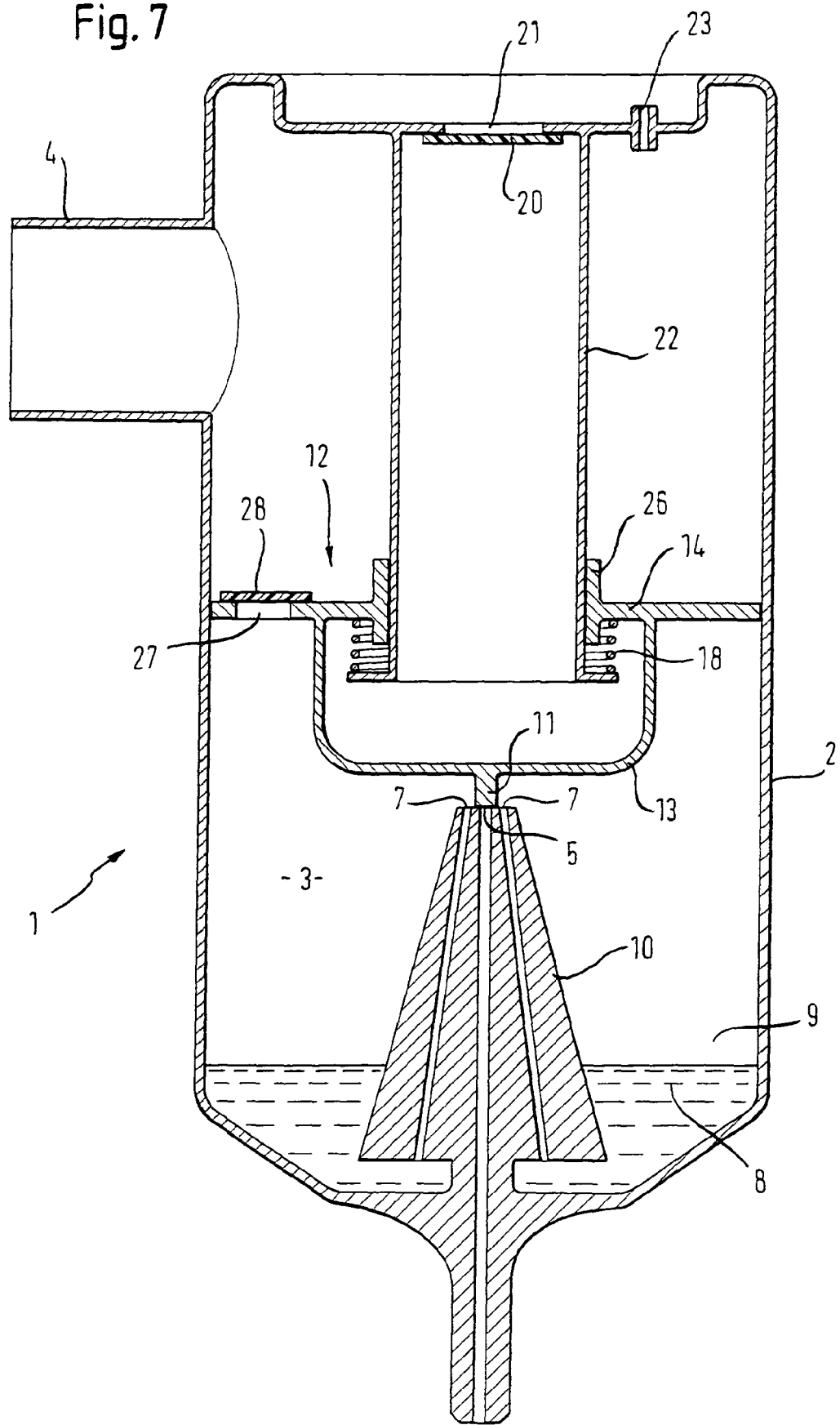
FIG. 7 shows a schematic sectional view of a further embodiment of an inhalation therapy device according to the invention.
Figure 8:
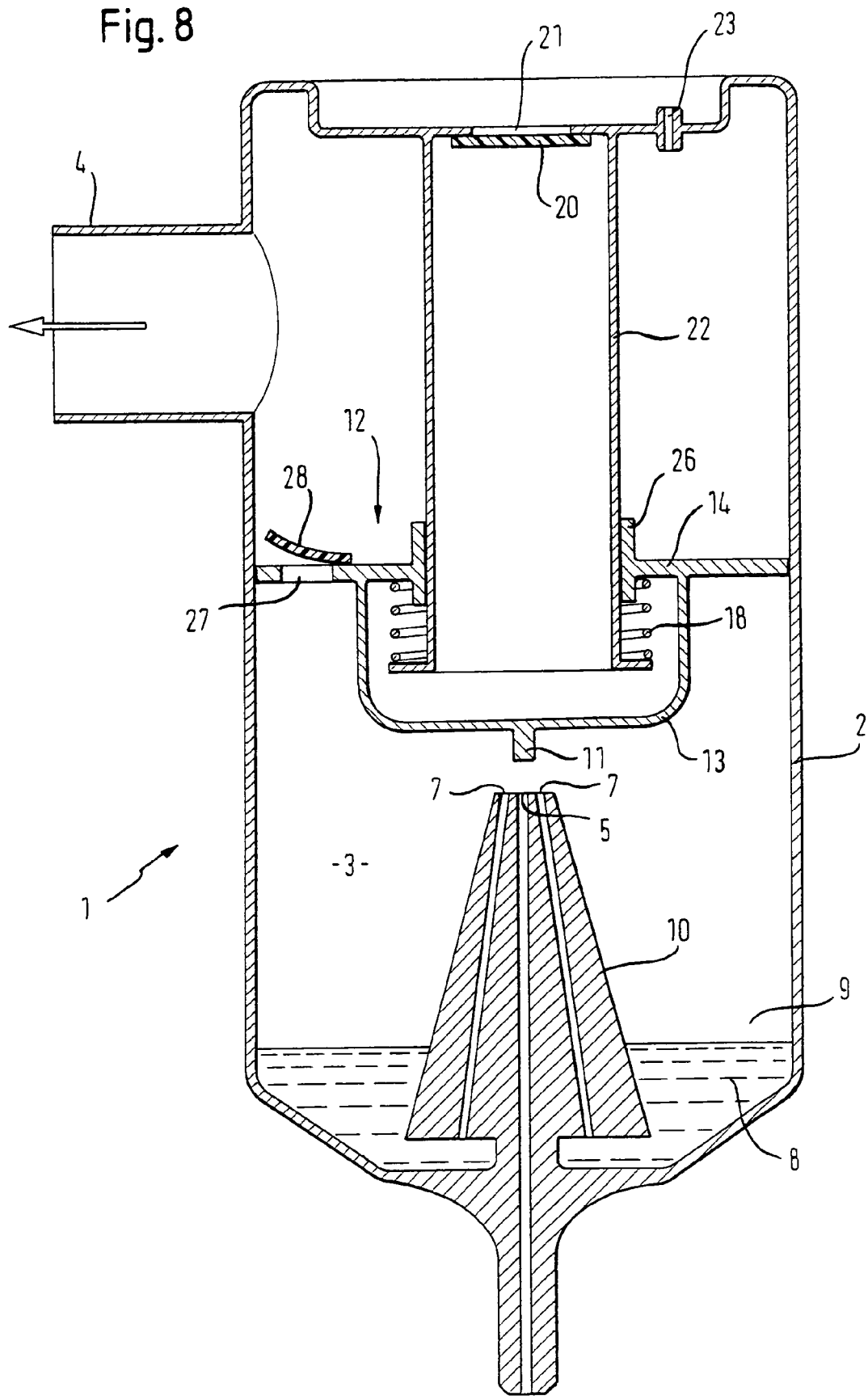
FIG. 8 shows a further schematic sectional view of the embodiment of FIG. 7.

FIGS. 7 and 8 show a further embodiment of an inhalation therapy device 1 according to the invention. An closing means 11 that can assume a position closing the nozzle opening, as shown in FIG. 7, and a position exposing the nozzle opening, as shown in FIG. 8, is also provided in this embodiment, the structure of which corresponds in many aspects to the embodiments described above such that reference can be made to the previous description. The closing means 11 is moved from one position into the other and back again by an actuation device 12.

The actuation device 12 comprises a connecting member 13 and a piston member 14 that is connected with the connecting member 13 and is disposed in a housing 2 of the device 1 in such a manner that it can move along the inner wall of the housing 2 as if it were in a cylinder. Deviating from the embodiments described above, the piston member is equipped with a sliding portion 26 in the embodiment of FIGS. 7 and 8, which surrounds a supply air duct 22 of the device 1 and gives the piston member 14 stability during its shifting movement. A spring member 18 is mounted on the supply air duct, which moves the piston member 14 into its rest position when the patient does not provide by exhalation into the device 1 a sufficient pressure in the interior of the device to shift the piston member 14 into the position shown in FIG. 7. When the piston member 14 is in this position, the closing means 11 that is connected with the connecting member is in the position blocking the nozzle opening.

In the inhalation phases, the piston member 14 moves into the position shown in FIG. 8 owing to the action of the spring member 18, such that the closing means 11 is in the position exposing the nozzle opening. Furthermore, during the inhalation phases, the aerosol together with the supply air that has flown in via the supply air duct flows through a through-hole 27 that is closed during the exhalation phases by means of a valve member 28. In the exhalation phases, the respiratory air flows through the respiratory air outlet opening 23 described in detail above; reference is herewith made to this description.

Figure 9A:
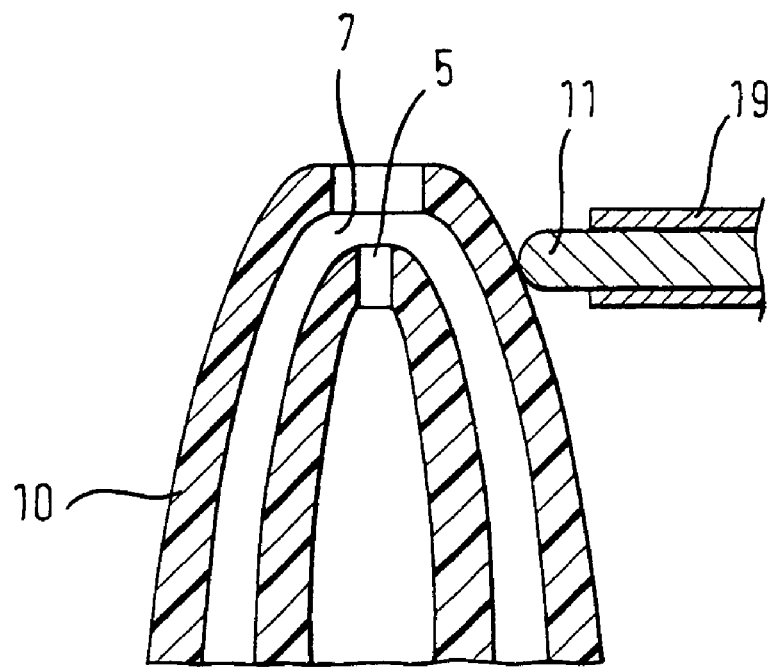
Figure 9B:
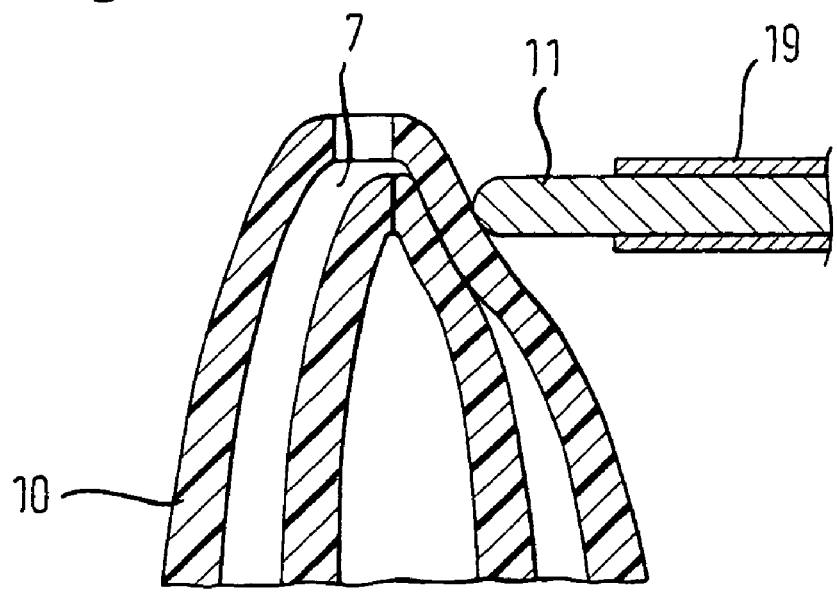

Shown in FIGS. 9A and 9B is a partial area of a further embodiment of an inhalation therapy device according to the invention, with essentially only those elements being shown in this section that are required to explain the differences to the embodiments described above. The differences will be dealt with in the following; reference is otherwise made to the above description.

In the embodiment according to FIGS. 9A and 9B, the closing means 11 is arranged to the side of a nozzle body 10 that is formed, at least partly, from a soft, flexible material. The nozzle body 10 comprises the nozzle opening 5 for the compressed air and the outlet opening 7 for the liquid to be nebulised, the outlet opening 7 being realised in the embodiment shown herein in the form of an annular gap surrounding the nozzle opening. The use of a soft, flexible material allows the nozzle body 10 to be deformed by the action of the closing means 11 to such an extent that the nozzle opening 5 is closed. Shown in FIG. 9B is the closing means 11 in the position closing the nozzle opening, into which the closing means 11 is brought by means of the actuation device 12 (not shown in FIG. 9B) depending on the breath of the patient. On the other hand, FIG. 9A shows the closing means 11 in the position exposing the nozzle opening. As is apparent, there is no deformation of the nozzle body 10 since the closing means is not acting on the nozzle body 10.

FIGS. 10A and 10B show a further embodiment of an inhalation therapy device according to the invention, with FIGS. 10A and 10B again also basically only showing those elements that are required to explain the differences to the embodiments described above. These differences will be dealt with in the following; reference is otherwise made to the above description.

Figure 10A:
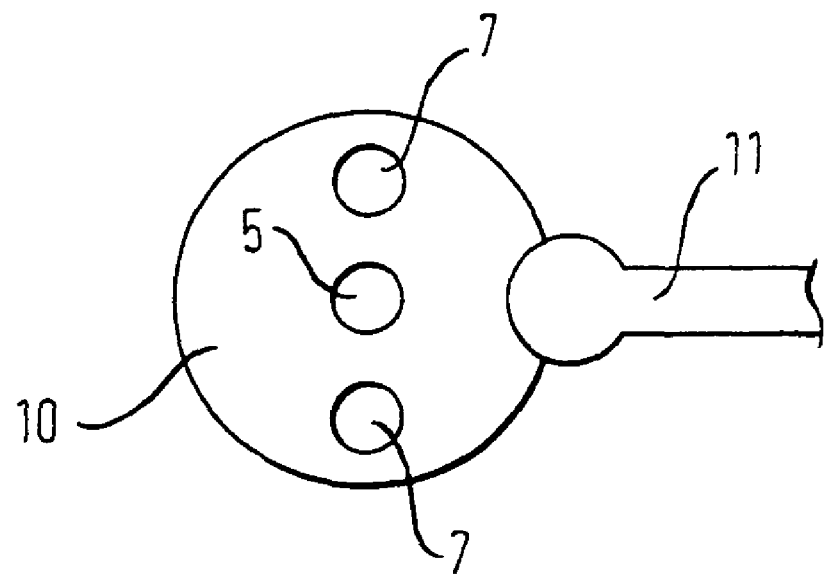
Figure 10B:
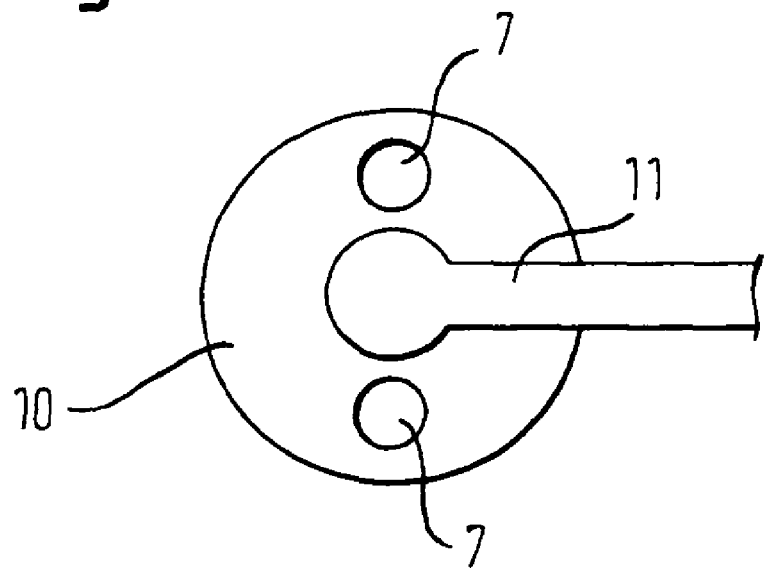

It must be noted with regard to FIGS. 10A and 10B that they show a top view of the nozzle head 10 with the nozzle opening 5 and the outlet openings 7. The symmetrical arrangement of the outlet openings 7 adjacent to the nozzle opening 5 as described above is clearly apparent. The closing means 11 is also disposed to the side of the nozzle head 10 in the embodiment according to FIGS. 10A and 10B. FIG. 10A shows the closing means 11 in the position exposing the nozzle opening 5, whereas the closing means 11 in FIG. 10B is shown in the position closing the nozzle opening. The closing means 11 is moved to and fro between these two positions by the actuation device 12 (which is not shown in FIGS. 10A and 10B) depending on the breath of the patient.

The invention claimed is:

1. Breath-controlled inhalation therapy device for the provision of an aerosol for use by a patient as part of an inhalation therapy, said device comprising
    a housing that defines a nebulisation area,
    a nozzle opening for the entry of a pressurised gas, preferably compressed air, into the nebulisation area,
    at least one outlet opening for the entry of a liquid to be nebulised, preferably a therapeutically effective liquid, into the nebulisation area,
    a closing means for closing the nozzle opening, which is arranged in the nebulisation area relative to the nozzle opening such that the closing means can be moved into a position closing the nozzle opening and into a position exposing the nozzle opening, and an actuation device for actuating the closing means in response to the respiratory cycle of the patient so as to actuate the closing means during the exhalation phase of a respiratory cycle of the patient such that the closing means assumes the position closing the nozzle opening.

2. An inhalation therapy device according to claim 1, wherein the closing means is disposed opposite the nozzle opening.

3. An inhalation therapy device according to claim 2, wherein in the position exposing the nozzle opening, the closing means forms a baffle for the compressed gas exiting out of the nozzle opening and the liquid exiting out of the outlet opening.

4. An inhalation therapy device according to claim 1, wherein the closing means is disposed to the side of the nozzle opening.

5. An inhalation therapy device according to claim 4, wherein the closing means for closing the nozzle opening acts on a nozzle body made of a soft, flexible material, in which the nozzle opening is formed.

6. An inhalation therapy device according to claim 1, wherein the closing means is made at least partly of a soft and flexible material.

7. An inhalation therapy device according to claim 1, wherein a sealing portion made of a soft and flexible material is provided at the nozzle opening.

8. An inhalation therapy device according to claim 1, wherein the actuation device comprises a connecting means that connects the actuation device to the closing means.

9. An inhalation therapy device according to claim 8, wherein the actuation device comprises a piston member, the pressure prevailing in the housing determining the position of the piston member.

10. An inhalation therapy device according to claim 9, wherein the actuation device comprises a spring member that determines the rest position of the piston member.

11. An inhalation therapy device according to claim 10, wherein the actuation device comprises a cylindrical member and wherein the spring member is disposed in the compression space that is enclosed by the piston member and the cylindrical member.

12. An inhalation therapy device according to claim 11, wherein the cylindrical member is formed by the housing.

13. An inhalation therapy device according to claim 9, wherein the connecting means is connected to the piston member.

14. An inhalation therapy device according to claim 13, wherein the connecting means is extended beyond the piston member such that the connecting member protrudes out of the housing.

15. An inhalation therapy device according to claim 9, wherein a ventilation passage is provided for the inlet of air to and the outlet of air from the space enclosed by the piston member and the cylindrical member during movement of the piston member in the cylindrical member.

16. An inhalation therapy device according to claim 8, wherein the actuation device comprises a guide member in which the connecting member is disposed.

17. An inhalation therapy device according to claim 8, wherein the connecting member is configured integrally with the closing means.

18. An inhalation therapy device according to claim 1, wherein the actuation device is disposed in a supply air duct of the inhalation therapy device.

* * * * *